United States Patent
Kerkhof

(10) Patent No.: US 7,078,057 B2
(45) Date of Patent: Jul. 18, 2006

(54) PROCESS FOR PRODUCING NANOMETER PARTICLES BY FLUID BED SPRAY-DRYING

(76) Inventor: Nicholas J. Kerkhof, 1604 E. FM 916, Rio Vista, TX (US) 76093

(*) Notice: Subject to any disclaimer, the term of this patent is extended or adjusted under 35 U.S.C. 154(b) by 626 days.

(21) Appl. No.: 10/168,520

(22) PCT Filed: Dec. 19, 2000

(86) PCT No.: PCT/US00/34606
§ 371 (c)(1),
(2), (4) Date: Oct. 18, 2002

(87) PCT Pub. No.: WO01/45677
PCT Pub. Date: Jun. 28, 2001

(65) Prior Publication Data
US 2003/0211162 A1    Nov. 13, 2003

Related U.S. Application Data

(60) Provisional application No. 60/172,573, filed on Dec. 20, 1999.

(51) Int. Cl.
| | |
|---|---|
| B29B 9/00 | (2006.01) |
| A61K 9/14 | (2006.01) |
| A61K 31/70 | (2006.01) |
| A61K 31/57 | (2006.01) |
| A61K 31/175 | (2006.01) |

(52) U.S. Cl. .................... 424/489; 514/23; 514/178; 514/464; 264/5

(58) Field of Classification Search ................ 242/480, 242/180.888
See application file for complete search history.

(56) References Cited

U.S. PATENT DOCUMENTS

| | | | |
|---|---|---|---|
| 3,771,237 A | 11/1973 | Hansen et al. ............... 34/57 A |
| 4,511,592 A | 4/1985 | Percel et al. ................. 426/646 |
| 4,689,297 A | 8/1987 | Good et al. .................. 435/171 |
| 4,851,421 A | 7/1989 | Iwasaki et al. .............. 514/352 |
| 4,885,848 A | 12/1989 | Christensen ................. 34/57 R |
| 5,006,204 A | 4/1991 | Jensen .......................... 159/3 |
| 5,015,480 A * | 5/1991 | Childers et al. ............. 424/486 |
| 5,133,137 A | 7/1992 | Petersen ..................... 34/57 A |
| 5,145,684 A | 9/1992 | Liversidge et al. ......... 424/489 |
| 5,325,606 A | 7/1994 | Liborius ...................... 34/589 |
| 5,357,688 A | 10/1994 | Christensen ................. 34/369 |
| 5,392,531 A | 2/1995 | Christensen et al. .......... 34/583 |
| 5,510,118 A | 4/1996 | Bosch et al. ................. 424/489 |
| 5,573,783 A * | 11/1996 | Desieno et al. .............. 424/490 |
| 5,591,733 A * | 1/1997 | Bolger et al. ................ 514/172 |
| 5,955,448 A * | 9/1999 | Colaco et al. ................. 514/53 |

FOREIGN PATENT DOCUMENTS

| | | |
|---|---|---|
| EP | 0411629 A2 | 2/1991 |
| EP | 411629 A3 | 2/1991 |
| EP | 0411629 B1 | 11/1993 |
| EP | 611567 A1 * | 8/1994 |
| WO | WO 9521617 | 8/1995 |
| WO | WO 9609814 | 4/1996 |
| WO | WO 9616076 | 5/1996 |
| WO | WO 9640628 | 12/1996 |
| WO | WO 97/13503 | 4/1997 |

OTHER PUBLICATIONS

Pharmaceutical Sciences 1990. Mack Publishing Company. pp. 1644-1647.
Krukonis. Supercritical Fluid Nucleation of Difficult-To-Comminute Solids. 1984.

* cited by examiner

*Primary Examiner*—Michael Hartley
*Assistant Examiner*—Nabila Ebrahim
(74) *Attorney, Agent, or Firm*—Morgan Lewis & Bockius

(57) ABSTRACT

Nanometer particles of poorly water-soluble or substantially water-insoluble compound are produced by finely-spraying a non-aqueous solution of said compound into a heated and fluidized bed of carrier excipient. The resulting product consists of a free flowing mixture of relatively large particles of carrier excipient and nanometer sized particles (less than 3 μm)) of compound.

21 Claims, No Drawings

PROCESS FOR PRODUCING NANOMETER PARTICLES BY FLUID BED SPRAY-DRYING

This patent application claims priority to Provisional Application No. 60/172,573 filed on Dec. 20, 1999 and International Application No. PCT/US00/34606 filed on Dec. 19, 2000.

BACKGROUND OF THE INVENTION

1. Field of the Invention

The present invention relates to methods for producing nanometer particles of compounds that are useful in pharmaceutical, food and cosmetic applications. Specifically, this invention is concerned with producing nanometer particles by utilizing a technique in which a solution of non-aqueous or mixed aqueous/non-aqueous solvent and a solute which is compound that is poorly soluble or substantially insoluble in water is finely sprayed and dried into a fluidized bed of one or more carrier excipients.

2. Related Art

Particles of compounds having low water-solubility are commonly used in a wide variety of applications, including ceramics, paints, inks, dyes, lubricants, pharmaceuticals, food products, pesticides, insecticides, fungicides, fertilizers, chromatography columns, cosmetics, lotions, ointments, and detergents. Aqueous dispersions of particles are used in many cases to avoid hazards such as flammability and toxicity associated with organic solvents. Such dispersions typically have a broad range of particle size.

In many cases product performance can be improved by controlling the particle size distribution. In general, smaller particles of a compound will dissolve faster than larger particles of the same compounds. Control of particle size is, therefore, important in controlling the rate of solubilization.

Obtaining particle sizes in the nanometer range is often useful for enhancing the effectiveness of compounds. This is particularly true for compounds that are practically insoluble or slightly soluble in water. Nanometer particles provide a large specific surface area, leading to increased dissolution rate and bioavailability of pharmaceutical drug substance, digestibility of food ingredients, as well as functional effectiveness of cosmetic ingredients. In particular, reducing the particle size of practically insoluble or poorly-soluble drug substances has been shown to increase the dissolution rate and consequently, their bioavailability.

A limited number of methods are known in the art for producing materials having nanometer particle sizes.

G. G. Liversidge et al., U.S. Pat. No. 5,145,684 issued on Sep. 8, 1992 describes a method for forming nanoparticles of a water-insoluble drug by wet milling in the presence of a surfactant. Wet bead milling, in which the material, suspended in aqueous medium, is milled by using glass, polymer, aluminum, zirconium or other metal beads. The milling process can be performed in a roller mill, vibratory mill or high energy mechanical mill. A dispersion consisting of a liquid dispersion medium and the above-described particles is described as being stable.

H. W. Bosch et al., "Process for Preparing Therapeutic Compositions Containing Nanoparticles," U.S. Pat. No. 5,510,118 issued on Apr. 23, 1996 describes a method for forming nanoparticles of a drug by high pressure homogenization. In this method, a suspension of the material is forced to pass through a narrow orifice by applying a high pressure. The high shear applied to the suspension reduces the particle size of the suspension.

V. Krukonis, "Supercritical Fluid Nucleation of Difficult-to-Comminute Solids," presented at the American Institute of Chemical Engineers, San Francisco, Nov. 25–30,1984, describes a method for forming nanoparticles of a drug using super-critical fluid technology. A solution of material in liquid carbon dioxide or in a mixture with another solvent is precipitated by reducing the applied pressure at a controlled rate to form particles of solid compound that have a nanometer size range.

With respect to wet bead milling, the batch size for roller or vibratory mills is limited by the size of the container on the mill. High energy mechanical milling is a continuous process capable of achieving nanometer particles in a short period of time. However, the beads are subjected to severe collisions with the metal chamber, such that abrasion could result in glass or metal contamination of the milled material.

The high pressure homogenization method described by Bosch et al. is usually used to reduce the size of liquid globules in dispersed systems, i.e., emulsions or liposomes. The success of high pressure homogenization method for solid materials is dependent on the physical property of the materials.

Super-critical fluid technology has at present a limitation in batch size. The feasibility of producing nanometer particles on a commercial scale has not yet been proven.

Iwasaki et al., U.S. Pat. No. 4,851,421 discloses biocidal fine powders containing particles with a diameter of 0.5 micron or less that are formed by wet milling a dispersion liquid of a biocidal substance with a rigid media having a particle diameter of 0.5 mm or less. Biocidal substances include germicides, herbicides, insecticides, miticides and tickicides that are water-insoluble. Iwasaki et al. also disclose that the resulting biocidal fine powder can more promptly permeate through the surfaces of plants as well into insect bodies and microbe cells.

European application EP 0 411629, published Feb. 6, 1991, describes a process whereby ultrafine particles of a slightly-soluble drug, whose average diameter is less than 2 to 3 µm, are obtained by milling the drug in the presence of a grinding aid selected from a sugar and a sugar alcohol. The weight ratio of said sugar or sugar alcohol is 2.5 to 50 parts by weight to one part of the drug, and the micronized drug has an average diameter of less than 1 µm.

A need continues to exist in the art for a method of producing nanometer particles of compounds, which method can conveniently be scaled up to production scale, and does not contaminate the final product with metals or glass.

Fluidized Bed Technology

Fluid bed technology is commonly used for drying and granulating pharmaceutical dosage forms. In fluid bed drying, a wet, granulated drug and excipients, produced by a high shear mixing, is fluidized with warm air to afford a dried granulation for further processing. In fluid bed granulation, a binder solution is sprayed into a heated and fluidized bed of drug-excipients blend to afford a dried granulation.

In general applications of the technology, powders are suspended in an upwardly moving column of air while at the same time a controlled and defined amount of liquid is injected into the powder stream to produce a moistened state or "agglomeration" of the powder; mild heat is then used to dry the agglomerated powder. Following this agglomeration, the powder has altered physical characteristics from the starting powder. For example, non-processed powder often produces significant dust when used, and dissolves poorly or slowly in various solvents, while agglomerated powder is substantially dust-free and dissolves rapidly.

Apparatuses for producing and/or processing particulate materials by fluid bed technology are available commercially (e.g., from Niro, Inc./Aeromatic-Fielder; Columbia, Md.), and are described, for example, in U.S. Pat. Nos. 3,771,237; 4,885,848; 5,133,137; 5,357,688; and 5,392,531; and in WO 95/13867. Such apparatuses have been used to prepare agglomerated powders of various materials, including milk whey (U.S. Pat. No. 5,006,204), acidulated meat emulsions (U.S. Pat. No. 4,511,592), proteases (U.S. Pat. No. 4,689,297), other proteins (DK 167090 B 1), and sodium bicarbonate (U.S. Pat. No. 5,325,606).

Spray Drying Technology

In a spray-drying process, a dispersion of solid particles is finely sprayed into flowing warm air to afford dried powder of the material. This technology does not reduce the particle size.

Spray drying consists of bringing together a highly dispersed liquid and a sufficient volume of hot air to produce evaporation and drying of the liquid droplets. In a typical spray drying process, the feed liquid may be a solution, slurry, emulsion, gel or paste, provided it is pumpable and capable of being atomized. A feed solution is sprayed into a current of warm, filtered air. The air supplies the heat for evaporation and conveys the dried product to a collector. The air is exhausted together with the moisture.

Spray-dried powder particles are homogeneous, approximately spherical in shape, nearly uniform in size. Lactose, mannitol, and flour are spray-dried for use in direct-compression tableting formulations. Remington's Pharmaceutical Sciences, 18th edition, Mack Publishing Company, Easton, Pa. (1990).

Spray drying has also been previously employed to microencapsulate active agents for drug delivery. This use of spray drying comprises spraying a mixed solution of active agent and a co-ingredient that is able to form a matrix or shell around the active agent. PCT published application WO96/09814, published Apr. 4, 1996, describes such a method to form spray-dried microparticles. One described embodiment is directed to microparticles comprising a low molecular weight drug and lactose. In one example, alcohol dehydrogenase (ADH) and lactose were spray dried to form microparticles (ADH 0.1% w/w; lactose 99.9% w/w). The microparticles were 4–5 μm in diameter, smooth and spherical, and contained air.

SUMMARY OF THE INVENTION

The present invention is based upon the discovery that a combination of fluid bed technology and spray-drying technology can be employed to form stable nanometer particles. Nanometer particles of poorly water-soluble or substantially water-insoluble compound are produced by finely-spraying a non-aqueous solution of said compound into a heated and fluidized bed of carrier excipient. The resulting product consists of a free flowing mixture of relatively large (up to 5 mm) particles of carrier excipient and nanometer-sized particle, i.e., nanoparticles (less than 3 μm) of compound.

A first aspect of the present invention relates to a method for producing nanometer particles of compounds that are useful in cosmetic, food and pharmaceutical applications. This process is particularly useful for drug substances which are poorly soluble or practically insoluble in water.

A second aspect of the present invention relates to providing a pharmaceutical formulation which comprises, as an active ingredient, drug particles having a size of less than 1000 nm, produced according to the above process, together with suitable excipients or diluents therefor.

The present invention allows for the large scale production of nanoparticles.

The present invention also results in nanoparticle compositions that are not contaminated with glass or metal from the formulation process.

The present invention optionally allows for the formation of stable nanoparticles without resorting to the addition of surface active agents during processing.

DETAILED DESCRIPTION OF THE PREFERRED EMBODIMENTS

The present invention is directed to a process for producing a mixture of nanometer particles of a poorly water soluble or substantially water-insoluble compound and a carrier excipient. The process comprises spraying a solution of a water-insoluble or poorly water soluble compound in at least one organic solvent into a fluidized bed of carrier excipient particles, under conditions that allow for a substantial amount of organic solvent to be removed from said solution, such that a mixture of carrier excipient and particles of said compound having a volume-weighted mean diameter i.e., particle size of less than or equal to 3000 nm is formed.

The process according to the present invention, is generally carried out by a) introducing a carrier excipient in the form of a dry powder, spray granules or microgranules into a fluidized bed drier in which the bed is kept at from about 20° to about 80° C., preferably about 25° to about 50° C., in particular about 27° to about 48° C.;

b) spraying onto the fluidized bed of excipient a non-aqueous or water-containing solution of a compound such that stable particles of compound exist in a mixture with the excipient, wherein said stable particles of compound have an average particle size of from about 50 nm to about 3000 nm, preferably from about 50 nm to about 1000 nm, more preferably about 200 nm to about 900 nm, most preferably about 300 nm to about 800 nm.

The resulting nanoparticles are stable and do not appreciably flocculate or agglomerate due to interparticle attractive forces. Preferably, the compound is a compound that is poorly water soluble or substantially water insoluble. The nanoparticles can be formulated into pharmaceutical, cosmetic and food compositions that exhibit high bioavailability.

By stable, it is meant that the dispersion exhibits no flocculation or particle agglomeration visible to the naked eye at least fifteen minutes, and preferablly, at least two days or longer after preparation.

The carrier excipient is preferably a highly water-soluble compound or polymer. The resulting mixture of water soluble carrier excipient, such as a sugar or sugar alcohol, and nanoparticle compound is advantageous because the carrier excipients can disperse into water, thereby increasing the dissolution rate of nanometer sized compounds in aqueous media.

Useful carrier excipients that can be employed in the fluidized bed for pharmaceutical compositions include, but are not limited to, saccharides, such as sugars and sugar alcohols (for example, lactose or sucrose, mannitol, or sorbitol), starches, flour, cellulose preparations and/or salts such as carbonates, bicarbonates and phosphates, for example, tricalcium phosphate or calcium hydrogen phosphate.

Sugars and sugar alcohols used as a carrier excipient include sugar or sugar alcohols having a molecular weight of less than 500, and capable of easily dispersing and dissolving in water, thereby improving dissolution rate of the active ingredient. Examples of sugars and sugar alcohols usable in the present invention include xylitol, mannitol, sorbitol, arabinose, ribose, xylose, glucose, mannose, galactose, sucrose, lactose, and the like. They can be used alone, or as a mixture of two or more of these compounds. The most preferable sugar is spray-dried lactose having a particle size range of from about 10 μm to about 3 mm.

In the process of the invention, one part by weight of an active ingredient is combined with about one (1) to about 50 parts, preferably about 2.5 to about 20 parts, more preferably about 5 to about 10 parts by weight, of an excipient.

The process of the present invention is preferably employed with materials intended for pharmaceutical, food and cosmetic applications. Examples of nutritional agents appropriate for formulation as particulate suspensions include: betacarotene, vitamin A, vitamin B2, vitamin D, vitamin E, and vitamin K.

The phrase "poorly water soluble or substantially water insoluble" for purposes of the present invention means that the compound dissolves in water, particularly at 20° C., at a concentration of 10 mg/ml or less, preferably 5 mg/ml or less, and most preferably less than about 1 mg/ml. When present in the form of large particles, these compounds are typically insufficiently absorbed at the gastrointestinal tract when they are administered in the form of conventional solid formulations.

Drugs that are insoluble or poorly soluble in water can have significant benefits when formulated using particle sizes of 3000 nm or less in diameter. Useful drug classes appropriate for formulation using nanoparticles includes: analgesics, anti-inflammatory agents, anthelmintics, anti-allergenics, anti-arrhythmic agents, antibiotics, anticoagulants, anticonvulsants/antiepileptics, antidepressants, antidiabetic agents, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, doparninergics, haemostatics, immunological agents, lipid regulating agents, muscle relaxants, parasympathomimetic, parathyroid calcitonin, prostaglandins, radio-pharmaceuticals, sex hormones, sleeping aids, stimulants, sympathomimetics, thyroid agents, vasodilators, and xanthines. The treatment of deficiency diseases, alcohol abuse, drug abuse, and many others could be improved with intravenous administration of particulate suspensions of the appropriate drug. Other medical applications for using nanoparticles will be apparent to those skilled in the art.

Specific examples of the slightly-soluble drugs are coronary vasodilators such as nifedipine, nicardipine, nimodipine, dipyridamole, disopyramide, prenylamine lactate, and efloxate; antihypertensives such as dihydroergotoxine and prazosin; steroidal anti-inflammatory agents such as cortisone, dexamethasone, betamethasone, and fluocinolone acetonide; non-steroidal anti-inflanu-natory agents such as indomethacin, naproxen, and ketoprofen; psychoneurotic agents such as phenytoin, phenacetamide, ethylphenacetamide, ethotoin, primidone, phensuximide, diazepam, nitrazepam, and clonazepam; cardiacs such as digoxin, digitoxin, and ubidecarenon; diuretics such as spironolactone, triamterene, chlorthalidone, polythiazide, and benzthiazide; chemotherapeutics such as griseofulvin, nalidixic acid, and chloramphenicol; skeletal muscle relaxants such as chlorzoxazone, phenprobamate, and carisoprodol; anticonvulsants such as etomidoline; neuroactive steroids and neuroactive semicarbazones as further described herein, antihistaminic agents such as diphenhydramine, promethazine, mequitezine, bisbenthiamine, and clemastine fumarate.

A preferred class of poorly soluble or practically insoluble drugs are steroids, especially neuroactive steroids. Neuroactive steroids are described in U.S. Pat. No. 5,591,733 and PCT published applications WO95/21617, published Aug. 17, 1995 and WO96/16076 published May 30, 1996. Most preferred neuroactive steroids are 3α-hydroxy-3β-methyl-5α-pregnan-20-one (ganaxolone), 3 α-hydroxy-3β-trifluoromethyl-19-nor-5β-pregnan-20-one, 2β-ethynyl-3α-hydroxy-5α-pregnan-20-one, and 3α,21-dihydroxy-3β-trifluoromethyl-19-nor-5β-pregnan-20-one. Another preferred class of drugs includes semicarbazones and thiosemicarbazones. Particularly useful semicarbazones are described in PCT published application WO96/40628. Most preferred semicarbazones are 4-(4fluorophenoxy)benzaldehyde semicarbazone and 4-(3,4-methylenedioxyphenoxy) benzaldehyde semicarbazone.

The compounds that are to be treated according to the invention can be dissolved in a non-aqueous solvent or mixed solvents, including mixtures of non-aqueous solvents as well as mixtures of non-aqueous and aqueous solvents. Useful non-aqueous solvents include alcohols, halogenated alkanes, dialkylketones and aromatic solvents. Examples of useful solvents include ethanol, preferably 95% ethanol, isopropyl alcohol, methylene chloride, chloroform, acetone, methylethyl ketone and toluene.

A mixture of non-aqueous solvents can be used to increase the solubility of the materials or to decrease the volatility of the solvent having a low boiling point.

The solution of materials that is to be sprayed may contain other substances that alter the release profile of the materials from the resulting nanometer particle product. These other substances include surface modifiers and surfactants.

When a surface modifier is used as an additional ingredient, the surface modifier is not subject to limitation, as long as its addition can lower the viscosity of the sprayed solution, improve solvent wetting during processing to prevent tile formation of "aggregates," or improve the absorption and uptake by the bodies of animals of poorly soluble active agents, such as drugs. Examples of useful surface modifiers include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene caster oil derivatives, polyoxyethylene sorbitan fatty acid esters, polyethylene glycols, polyoxyethylene stearates, colloidol silicon diokide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

The process of the present invention can be practiced with commercially available fluid-bed apparatuses that are equipped with an insert for top spray or bottom spray using a Wurster-type column, or tangential spray using a rotor disk. The design and operation of the sprayer can vary many characteristics of the final product, such as particle size and size distribution, bulk and particle densities, porosity, moisture content, flowability and friability. In the present invention, the design and operation of the sprayer must be such to ensure that the dried particles of compound have an average particle size of less than or equal to 3 microns, preferably less than or equal to 2 microns, more preferably less than or equal to 1 micron. Exemplary conditions are provided for a particular apparatus below. In view of this guidance, one of ordinary skill in the art will be able to adjust apparatus and process parameters to achieve similar results with other fluid-bed/sprayer combinations that are available in the art.

Other suitable apparatus will be apparent to those of skill in the art. A suitable apparatus should have multiple functions as described below. Examples include Wurster fluidized bed granulation coaters (such as those produced by Glatt K. K. or Powrex Corporation). This apparatus, which has a cylindrical Wurster column set at the center of a container, is typically employed to fluidize a fine powder or a granulated particle through the column in a single direction by an upward gas stream (jet stream), spray fine droplets of a binder or those of a binder and a surfactant to the subject particle from the jet nozzle at the bottom for coating (bottom spray method) and perform granulation and drying.

In addition to the above-described apparatus, multi-function, combined granulation coaters of the agitating tumbling fluidized bed type (e.g, SPJR-A FLOW granulation coater, produced by Freund Industrial Co., Ltd., and New Marumerizer, produced by Fuji Paudal Co., Ltd.), multi-function combined granulation coaters of the tumbling fluidized bed type (e.g., Multiplex, produced by Powrex Corporation) and other apparatuses can also be used. Spraying methods of these multi-function, combined granulation coaters include the top spraying method, in which droplets are sprayed from the top, the middle spraying (tangential spraying) method, in which droplets are sprayed from a side of the bottom, and the bottom spraying method.

In the process of the present invention, a suitable excipient, such as spray-dried lactose, is fluidized by an upward gas stream. Fine droplets of a solution of water insoluble or poorly soluble agent are sprayed from a jet nozzle into the fluidized bed of lactose particles. As will be appreciated the gas stream is heated to allow the evaporation of the solvent from the sprayed solution. Rather than result in granulation and the formation of larger fluidized particles, the use of this apparatus in the present invention is to place a plurality of nanometer sized particles onto a carrier excipient in the fluid bed.

A useful bench top system for performing the process of the present invention is the Vector FL-M-1 fluid bed system equipped with a 6 inch Wurster column. Useful spray rates are from about 25 to about 50 mL/min, preferably about 30 to about 45 mL/min, most preferably from about 34 to about 41 mL/min using one or more spraying nozzles. Static inlet pressure should be controlled to be in the range of about 2 to about 10 bar, preferably about 2.5 to about 8 bar (about 250 to about 800 kPa) affording an air flow of about 20 to about 50 cfm, preferably about 25 to about 45 cfm. Inlet temperature should be about 80° C. to about 100° C., preferably about 85° C. to about 90° C. Product temperature should be about 20° C. to about 60° C., preferably about 25° C. to about 50° C., most preferably about 27° C. to about 48° C.

It is necessary to control the apparatus to preventing flocking (aggregation) of the subject carrier excipient, and aggregation of the sprayed particles during the process by minimizing the diameter of the droplets of solution of compound that is sprayed, and increasing the speed at which the droplets collide with the carrier excipient particles during spraying and drying. A suitable surfactant can be employed in the solution of compound to aid in processing.

The concentration/amount of compound, solvent(s), and optional surfactant used for such spraying are optionally chosen so that the resulting compound particles have the desired particle size of not more than 3 microns, preferably less than or equal to 2 microns, more preferably less than or equal to 1 micron.

The particles preferably have a volume-weighted mean diameter of less than 3000 nm, preferably from about 50 nm to about 2000 nm, more preferably about 50 nm to about 1000 nm, even more preferably about 200 nm to about 900 nm, most preferably about 300 to about 800 nm.

For purposes of the present invention, particle size in the mixtures is determined by a laser diffraction technique using photo correlation spectroscopy (Nicomp C370). The results are reported in terms of volume-weighted mean diameter. Volume-weighted mean diameter is defined as follows:

$$(\Sigma nd^4)/(\Sigma nd^3)$$

where n=the number of particles in a size interval characterized by a diameter "d". Remington's Pharmaceutical Sciences, 18th edition, Mack Publishing Company, Easton, Pa. (1990).

The micronized drug obtained by the invention can be formulated in the form of powders, tablets, granules, capsules, aerosols, suspensions, syrups, ointments, suppositories, and the like, with one or more additional pharmaceutically acceptable excipients and/or diluents.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

Suitable excipients, in addition to the "carrier excipient" are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the nanoparticle active compounds attached to carrier excipient particles that may be further mixed with fillers such as lactose, binders such as starches, and/or lubricants such as talc or magnesium stearate and, optionally, stabilizers. In soft capsules, the active compounds are preferably suspended in suitable liquids, such as, fatty oils or liquid paraffin. In addition, stabilizers may be added.

In a most preferred embodiment, a solution of the drug substance, ganaxolone, in ethanol (alcohol USP) is finely sprayed into a heated and fluidized bed of spray-dried lactose NF. The ganaxolone is deposited in the lactose in nanometer particle size.

The following examples are illustrative, but not limiting, of the method and compositions of the present invention. Other suitable modifications and adaptations of the variety of conditions and parameters normally encountered. and obvious to those skilled in the art are within the spirit and scope of the invention.

EXAMPLE I

Formation of Ganaxolone Nanoparticles in Admixture with Lactose

Approximately 100 g of ganaxolone was dissolved in 5 kg of ethanol with slight warming to 30° C. The solution was sprayed into 1 kg of spray-dried lactose NF (Fast Flo #316) in a Vector FL-M-1 fluid bed system equipped with a 6" Wurster column. The spray rate was 34–41 mL/min using one gun. The static inlet pressure was 2.5–8 bar (250–800 kPa) affording an air flow of 25–45 cfm. The inlet temperature was 85–90° C. and the product temperature was 27–48° C. The resulting ganaxolone powder mixture was free-flowing and contained 63 mg ganaxolone per g of powder. The ganaxolone particle size in the mixture was determined by a laser diffraction technique using photo correlation spectroscopy (Nicomp C370). The results showed that the ganaxolone had a volume-weighted mean diameter of 660 nm.

EXAMPLE 2

Bioavailability of Ganaxolone Nanoparticles

The spray-dried ganaxolone-lactose powder was tested for its bioavailability in dogs, in comparison with ganaxolone-β-cyclodextrin complex suspension which has been shown to afford clinical efficacy in epileptic patients. The maximum plasma concentration and the plasma area-under-the-curve of the nanometer spray dried ganaxolone-lactose powder were 72.5% and 90%, respectively, of those afforded by the ganaxolone-β-cyclodextrin complex suspension.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A process for producing a mixture of nanometer particles of a poorly water soluble or substantially water-insoluble pharmaceutical compound and a carrier excipient, said process comprising, spraying a solution of a water-insoluble or poorly water soluble pharmaceutical compound in at least one organic solvent into a fluidized bed of carrier excipient particles, under conditions that allow for a substantial amount of organic solvent to be removed from said solution, such that a mixture of particles of said pharmaceutical compound having a volume-weighted mean diameter of less than or equal to 3000 nm and of carrier excipient is formed.

2. The process of claim 1, wherein said particles of said pharmaceutical compound have a volume-weighted mean diameter from about 1000 nm to about 2000 nm.

3. The process of claim 1, wherein said particles of said pharmaceutical compound have a volume-weighted mean diameter of less than 1000 nm.

4. The process of claim 1, wherein the resulting particles of pharmaceutical compound have a volume-weighted mean diameter of about 50 nm to about 1000 nm.

5. The process of claim 1, wherein the resulting particles of pharmaceutical compound have a volume-weighted mean diameter of about 300 to about 800 nm.

6. The process of claim 1, wherein the pharmaceutical compound is dissolved in a liquid medium comprising at least one non-aqueous solvent prior to spraying.

7. The process of claim 6, wherein said solution further comprises an aqueous solvent.

8. The process of claim 1, wherein said pharmaceutical compound is selected from analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasodilators and xanthines.

9. The process of claim 1, wherein said pharmaceutical compound is a steroid.

10. The process of claim 9, wherein said pharmaceutical compound is a neuroactive steroid.

11. The process of claim 10, wherein said neuroactive steroid is selected from the group consisting of 3α-hydroxy-3β-methyl-5α-pregnan-20-one (ganaxolone), 3α-hydroxy-3β-trifluoromethyl-19-nor-5β-pregnan-20-one, 2β-ethynyl-3α-hydroxy-5α-pregnan-20-one, and 3α,21-dihydroxy-3α-trifluoromethyl-19-nor-5β-pregnan-20-one.

12. The process of claim 1, wherein said pharmaceutical compound is a semicarbazone or thiosemicarbazone.

13. The process of claim 12, wherein said semicarbazone is selected from the group consisting of 4-(4-fluorophenoxy) benzaldehyde semicarbazone and 4(3,4-methylenedioxyphenoxy) benzaldehyde semicarbazone.

14. The process of claim 1, wherein the weight ratio of said excipient is one to 50 parts by weight to one part by weight of the pharmaceutical compound.

15. The process of claim 1, wherein said excipient is a sugar or sugar alcohol having a molecular weight of less than 500.

16. The process of claim 15, wherein said sugar or sugar alcohol is selected from the group consisting of xylitol, mannitol, sorbitol, arabinose, ribose, xylose, glucose, mannose, galactose, sucrose and lactose.

17. The process of claim 16, wherein said excipient is lactose.

18. The process of claim 1, wherein said spraying occurs from one or more spraying nozzles in a fluid-bed apparatus equipped with an insert for (a) top spray using a Wurster-type column, (b) bottom spray using a Wurster-type column, or (c) tangential spray using a rotor disk.

19. The process of claim 1, wherein said solution of the pharmaceutical compound further comprises one or more other substances that alter the release profile of the compound from the resulting particles.

20. The process of claim 19, wherein said one or more other substances are selected from the group consisting of gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene caster oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

21. The process of claim 1, wherein said at least one organic solvent is a mixture of non-aqueous solvents that is used to increase the solubility of the pharmaceutical compound or to decrease the volatility of one of said mixture of solvents having a low boiling point.